(12) United States Patent
Misawa et al.

(10) Patent No.: US 12,422,663 B2
(45) Date of Patent: Sep. 23, 2025

(54) CAMERA HEAD AND IMAGING SYSTEM

(71) Applicant: TANAKA ENGINEERING INC., Saitama (JP)

(72) Inventors: Motohiro Misawa, Saitama (JP); Susumu Yagi, Saitama (JP)

(73) Assignee: TANAKA ENGINEERING INC., Saitama (JP)

( * ) Notice: Subject to any disclaimer, the term of this patent is extended or adjusted under 35 U.S.C. 154(b) by 0 days.

(21) Appl. No.: 19/105,607

(22) PCT Filed: Oct. 18, 2024

(86) PCT No.: PCT/JP2024/037275
§ 371 (c)(1),
(2) Date: Feb. 21, 2025

(87) PCT Pub. No.: WO2025/089207
PCT Pub. Date: May 1, 2025

(65) Prior Publication Data
US 2025/0264711 A1    Aug. 21, 2025

(30) Foreign Application Priority Data
Oct. 26, 2023 (JP) ................................. 2023-183689

(51) Int. Cl.
*G02B 23/24* (2006.01)
*H04N 23/50* (2023.01)
*H04N 23/56* (2023.01)

(52) U.S. Cl.
CPC ..... *G02B 23/2469* (2013.01); *G02B 23/2423* (2013.01); *G02B 23/2484* (2013.01); *H04N 23/555* (2023.01); *H04N 23/56* (2023.01)

(58) Field of Classification Search
CPC ............ G02B 23/2469; G02B 23/2423; G02B 23/2484; H04N 23/56; H04N 23/555
(Continued)

(56) References Cited

U.S. PATENT DOCUMENTS

2012/0010465 A1    1/2012   Erikawa et al.
2013/0289373 A1*  10/2013   Yamamoto ........... A61B 5/1459
                                                           600/339
(Continued)

FOREIGN PATENT DOCUMENTS

JP    H02110505 A  *  4/1990
JP    2005124776 A  *  5/2005
(Continued)

OTHER PUBLICATIONS

International Search Report dated Dec. 10, 2024 issued in International Patent Application No. PCT/JP2024/037275, with English translation.
(Continued)

*Primary Examiner* — James T Boylan
(74) *Attorney, Agent, or Firm* — Rimon P.C.

(57) ABSTRACT

In some cases, it is desirable for a camera head to be small. A camera head has an elongated shape, and is used for imaging an imaging area located in a vicinity of a leading end portion in a longitudinal direction. The camera head includes: a camera module; two or more light source units disposed at positions farther from the leading end portion than the camera module is in the longitudinal direction; and a light guide unit disposed radially outside an outer surface of the camera module and configured to guide light emitted from each of the two or more light source units to the vicinity of the leading end portion so that the imaging area is irradiated with the light, and at least two light source units of the two or more light source units are located at different positions in the longitudinal direction. With such a configuration, the camera head can be made even smaller.

20 Claims, 12 Drawing Sheets

(58) Field of Classification Search
USPC .......................................................... 348/68
See application file for complete search history.

(56) References Cited

U.S. PATENT DOCUMENTS

2014/0296638 A1  10/2014  Komukai
2019/0004308 A1   1/2019  Iwama
2023/0200635 A1   6/2023  Ishizuka et al.

FOREIGN PATENT DOCUMENTS

| JP | 2005-204944 A | | 8/2005 |
| JP | 4530128 B2 | | 8/2010 |
| JP | 2012-016545 A | | 1/2012 |
| JP | 2012205849 A | * | 10/2012 |
| JP | 6020870 B1 | | 11/2016 |
| JP | 6055691 B2 | | 12/2016 |
| JP | 6995659 B2 | | 1/2022 |
| JP | 7100171 B2 | | 7/2022 |
| WO | 2013/094569 A1 | | 6/2013 |
| WO | 2016/098444 A1 | | 6/2016 |

OTHER PUBLICATIONS

Notice of reasons for refusal of the corresponding Japanese Patent Application No. 2023-183689 issued on Jan. 23, 2024, with English Translation.

Notice of reasons for refusal of the corresponding Japanese Patent Application No. 2024-021041 issued on May 7, 2024, with English Translation.

Decision to Grant of the corresponding Japanese Patent Application No. 2023-183689 issued on Apr. 23, 2024, with English Translation.

* cited by examiner

CAMERA HEAD AND IMAGING SYSTEM

CROSS-REFERENCE TO RELATED APPLICATIONS

This application is the U.S. National Phase under 35 U.S.C. § 371 of International Patent Application No. PCT/JP2024/037275, filed on Oct. 18, 2024, which in turn claims the benefit of Japanese Patent Application No. 2023-183689, filed on Oct. 26, 2023, the entire disclosures of which Applications are incorporated by reference herein.

TECHNICAL FIELD

The present invention relates to a camera head and an imaging system used to image an imaging area in the vicinity of a leading end portion in a longitudinal direction.

BACKGROUND ART

Conventionally, various types of camera heads have been used in endoscopes for observing living organisms, industrial endoscopes, and the like. Some camera heads have a structure for emitting illumination light, and a camera module.

To reduce the diameter of such camera heads, some have a structure in which a light source is disposed behind the imaging module and a light guide guides light from the light source to the leading end (for example, see Patent Documents 1, 2, 3, 4, and 5 below).

Note that some camera heads have a structure in which a plurality of light guides and light emitters are disposed at equal intervals around the imaging element (for example, see Patent Documents 6, 7, and 8 below).

BACKGROUND ART

Patent Document

Patent Document 1: JP 6995659B
Patent Document 2: JP 2005-204944A
Patent Document 3: JP 4530128B
Patent Document 4: JP 2012-205849A
Patent Document 5: JP 02-110505A
Patent Document 6: JP 7100171B
Patent Document 7: JP 6020870B
Patent Document 8: JP 6055691B

SUMMARY OF INVENTION

Technical Problem

If a camera head can be downsized, the camera head and the imaging system using the camera head will become more useful in several applications.

The present invention aims to provide a smaller camera head and imaging system.

Solution to Problem

A camera head according to a first aspect of the present invention is a camera head that has an elongated shape and is used for imaging an imaging area located in a vicinity of a leading end portion in a longitudinal direction, including: a camera module; two or more light source units disposed at positions farther from the leading end portion than the camera module is in the longitudinal direction; and a light guide unit disposed radially outside an outer surface of the camera module and configured to guide light emitted from each of the two or more light source units to the vicinity of the leading end portion so that the imaging area is irradiated with the light, wherein at least two light source units of the two or more light source units are disposed at different positions in the longitudinal direction.

With such a configuration, the camera head that can irradiate the imaging area with light from the two or more light source units can be made smaller.

A camera head according to a second aspect of the present invention is the camera head according to the first aspect of the invention, wherein at least two light source units of the two or more light source units are configured to emit light of wavelengths different from each other.

With such a configuration, the camera head capable of irradiating the imaging area with light of multiple wavelengths can be made smaller.

A camera head according to a third aspect of the present invention is the camera head according to the first or second aspect of the invention, the light guide unit includes two or more optical fibers respectively corresponding to at least two light source units of the two or more light source units, and the two or more optical fibers are disposed around the camera module so as to be spaced apart from each other in a circumferential direction and lined up in the circumferential direction.

With such a configuration, the imaging area can be uniformly irradiated with the light from the light source units.

A camera head according to a fourth aspect of the present invention is the camera head according to the third aspect of the invention, wherein, of the two or more optical fibers, two or more optical fibers provided for guiding light within one wavelength band are disposed around the camera module so as to be spaced apart from each other in the circumferential direction, and the light guide unit is configured to irradiate the imaging area with the light within the one wavelength band from two or more positions that are spaced apart from each other in the circumferential direction.

With such a configuration, the imaging area can be uniformly irradiated with the light within the one wavelength band.

A camera head according to a fifth aspect of the present invention is the camera head according to the third or fourth aspect of the invention, wherein the camera module has a columnar portion having a polygonal columnar shape, and the two or more optical fibers are disposed along planar side surfaces of the columnar portion.

With such a configuration, the camera head can be made even smaller.

A camera head according to a sixth aspect of the present invention is the camera head according to any one of the first to fifth aspects of the invention, further including a sleeve formed into a tubular shape, wherein the camera module, the light source units, and the light guide unit are housed in the sleeve.

With such a configuration, a camera head that is small and easy to manufacture can be formed.

A camera head according to a seventh aspect of the present invention is the camera head according to any one of the first to fifth aspects of the invention, further including a sleeve formed into a tubular shape, wherein the sleeve is a light transmissive member, the light guide unit is a portion or an entirety of the sleeve, and the camera module is housed in the sleeve.

With such a configuration, the camera head can be made even smaller.

A camera head according to an eighth aspect of the present invention is the camera head according to any one of the first to seventh aspects of the invention, wherein the camera module and the light guide unit are integrated into one piece.

With such a configuration, a camera head that is small and easy to manufacture can be formed.

A camera head according to a ninth aspect of the present invention is the camera head according to any one of the first to eighth aspects of the invention, wherein, of the two or more light source units, at least two light source units located at different positions in the longitudinal direction are disposed so as to partially overlap each other when viewed from a front in the longitudinal direction.

With such a configuration, a camera head with at least two light source units can be reliably made smaller.

An imaging system according to a tenth aspect of the present invention is the imaging system according to any one of the first to ninth aspects of the invention, including: a camera head; and an image acquisition device connected to the camera head and configured to acquire an image captured by the camera head.

With such a configuration, an image can be acquired using a small camera head capable of irradiating the imaging area with the light from the two or more light source units.

Advantageous Effects of Invention

According to the present invention, it is possible to provide a smaller camera head and imaging system.

DESCRIPTION OF EMBODIMENTS

Figure 1:
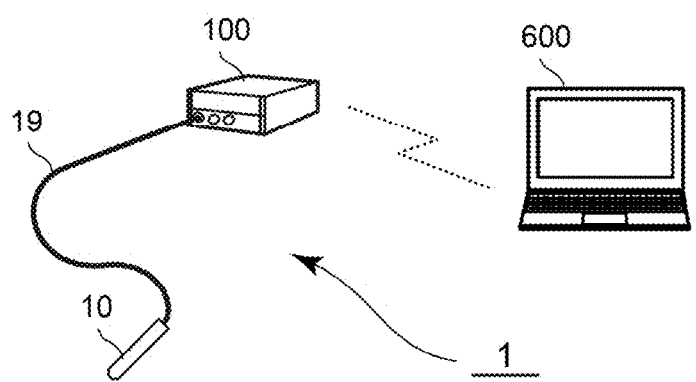
FIG. 1 is a diagram illustrating a configuration of an imaging system according to one embodiment of the present invention.

Hereinafter, an embodiment of a camera head, an imaging system using the same, and the like will be described with reference to the drawings. In the embodiment, components with the same reference numerals perform similar operations, and therefore repeated explanations may be omitted.

In the following description, the direction orthogonal to the longitudinal direction of the tubular camera head may also be referred to as a radial direction, and the direction along an arc centered around the central axis of the camera head extending in the longitudinal direction may also be referred to as a circumferential direction. In addition, in the following description, the direction toward the leading end portion in the radial direction may also be referred to as a "front" and the opposite direction may also be referred to as a "rear". For example, the shape and positional relationships of each unit may be described by indicating a particular direction in this way, but the explicit direction is only for ease of description and does not limit the orientation or posture of each device, etc., according to the present invention when used. In addition, expressions indicating a direction or expressions indicating a state such as horizontal, vertical, orthogonal, etc., only indicate that they can be roughly understood in that way, and do not necessarily have to be interpreted strictly as expressed.

Embodiment

The summary of the embodiments is as follows. The camera head is for imaging an imaging area in the vicinity of the leading end in the longitudinal direction. The camera head has a structure in which at least two light source units are disposed at different positions in the longitudinal direction farther from the leading end than the camera module is. The at least two light source units are preferably configured to emit light of wavelengths different from each other. Hereinafter, a camera head with such a configuration and the configuration of an imaging system using the camera head will be described.

Figure 2:
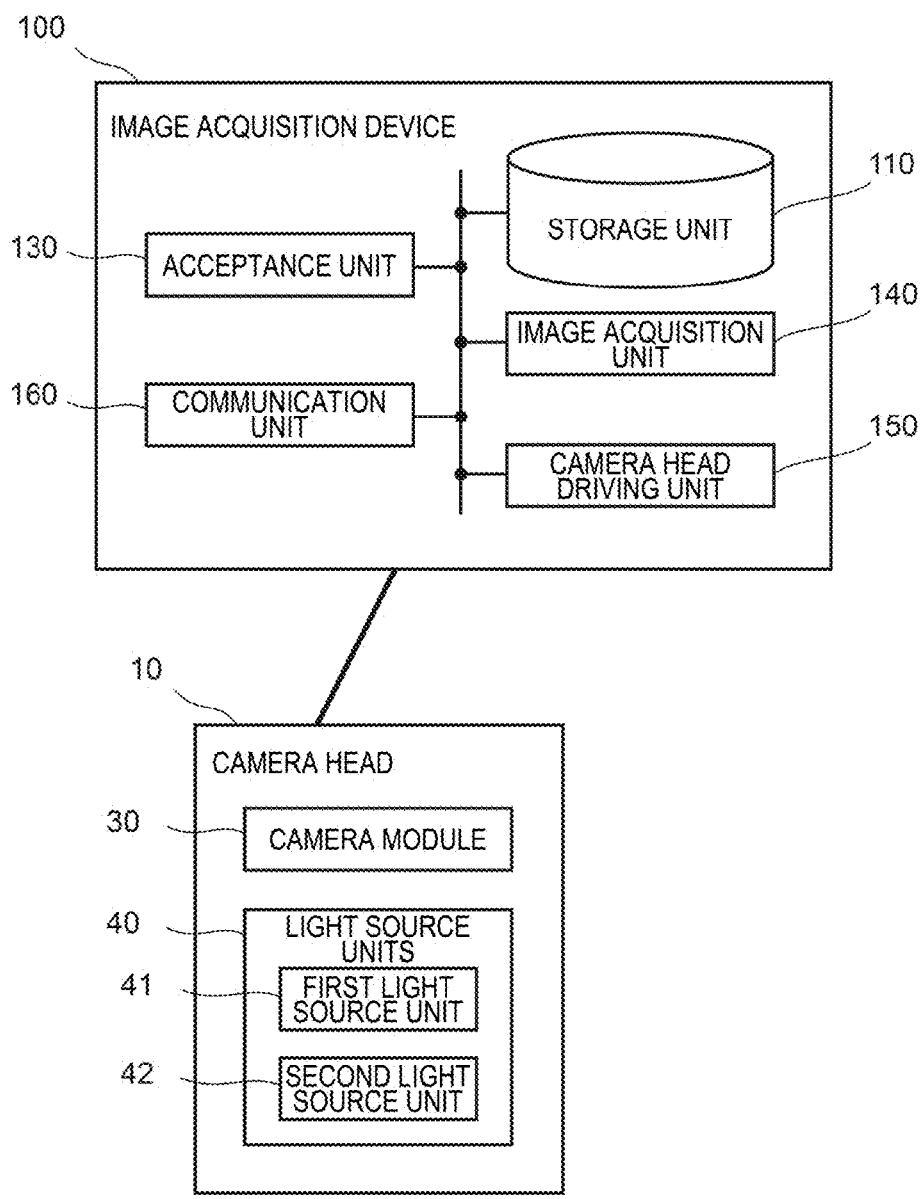
FIG. 2 is a block diagram of the imaging system according to the same.

FIG. 1 is a diagram illustrating a configuration of an imaging system 1 according to one embodiment of the present invention. FIG. 2 is a block diagram of the imaging system 1 according to the same.

As shown in the figures, the imaging system 1 includes a camera head 10 and an image acquisition device 100. The imaging system 1 can be used as an endoscope for observing and inspecting various organs of living organisms, an industrial endoscope, or the like. The imaging system 1 may also be referred to as an imaging device. The use of the imaging system 1 is not limited to the application described above. The imaging system 1 is configured to be capable of acquiring imaging results of an imaging area in the vicinity of the leading end of the camera head 10. The imaging system 1 is configured to be capable of recording the imaging results as images and outputting them to an internal or external output device.

Note that the images may be still images or moving images. A moving image may be considered to include a plurality of still images. In addition, there is no limitation on the format of the data recorded or output as images.

The expression "(to) output to an output device" includes displaying on a display or the like, printing on a medium using a printer or the like, transmitting information to another device via a network, etc.

The camera head 10 includes a camera module 30 and light source units 40. In the present embodiment, the light source units 40 include, for example, first light source units 41 and second light source units 42 that emit light of wavelengths different from each other. More types of light sources may be used. Further details of the structure of the camera head 10 will be described later.

The camera head 10 is connected to the image acquisition device 100 via a cable 19. The cable 19 includes, for example, a signal line for communicating with the camera module 30, electrical wires for supplying power for driving the camera module 30 and the light source units 40, and so on. The cable 19 is configured to be flexible, but is not limited to such a configuration.

The image acquisition device 100 is, for example, a device including a computer and configured to be capable of driving the camera head 10 to capture images. In the present embodiment, the image acquisition device 100 is configured to be capable of recording the imaging results and outputting the imaging results to an external terminal device 600 or the like and displaying them on a display of the terminal device 600 or the like. The image acquisition device 100 may have its own display and may be configured to be capable of displaying captured images. The image acquisition device 100 may be, for example, a personal computer itself or the like. In the present embodiment, the imaging system 1 may be understood to include the terminal device 600.

In the present embodiment, the image acquisition device 100 includes, for example, a storage unit 110, an acceptance unit 130, an image acquisition unit 140, a camera head driving unit 150, and a communication unit 160.

The storage unit 110 is preferably a non-volatile recording medium, but may also be realized as a volatile recording medium. The storage unit 110 stores each piece of information acquired by the image acquisition device 100. The process in which information or the like is stored is not limited to any specific process. For example, information or the like may be stored via a recording medium, information or the like transmitted via a communication line or the like may be stored, or information or the like input via an input device may be stored.

The acceptance unit 130 accepts the imaging results from the camera head 10, information or the like received by the communication unit 160, etc. as information input to the image acquisition device 100. The accepted information is accumulated temporarily or for the long term in the storage unit 110, or is used in the processing by the other units.

Note that the acceptance unit 130 may be capable of receiving information input from an input means. The input means may be any means, such as a numeric keypad, a keyboard, a mouse, or a menu screen. In this case, the acceptance unit 130 can be realized by a device driver for an input means such as a numeric keypad or a keyboard, or control software or the like for a menu screen.

The image acquisition unit 140 acquires images captured by the camera head 10. That is, the imaging results acquired by the camera module 30 of the camera head 10 and transmitted to the image acquisition device 100 via the cable 19 are acquired as images. The image acquisition unit 140 is configured to be capable of recording the acquired images in the storage unit 110.

The camera head driving unit 150 is configured to supply power to the camera module 30 and the light source units 40 of the camera head 10, to drive each unit, and to control the operation of each unit.

The image acquisition unit 140 and the camera head driving unit 150 are configured to be capable of operating, for example, by a computer executing a predetermined control program, but are not limited to to such a configuration.

The communication unit 160 connects the image acquisition device 100 to an external device so as to be able to communicate with each other. The communication unit 160 is realized, for example, by a wireless or wired communication means, but may also be realized by a means for receiving broadcast or a broadcasting means. In the present embodiment, the communication unit 160 is configured to be capable of communicating with, for example, an external terminal device 600 or the like, and transmitting images, which are imaging results of the camera head 10, to the terminal device 600. That is to say, the image acquisition device 100 is capable of outputting images captured using the camera head 10.

Next, the structure of the camera head 10 according to the present embodiment will be described.

Figure 3:
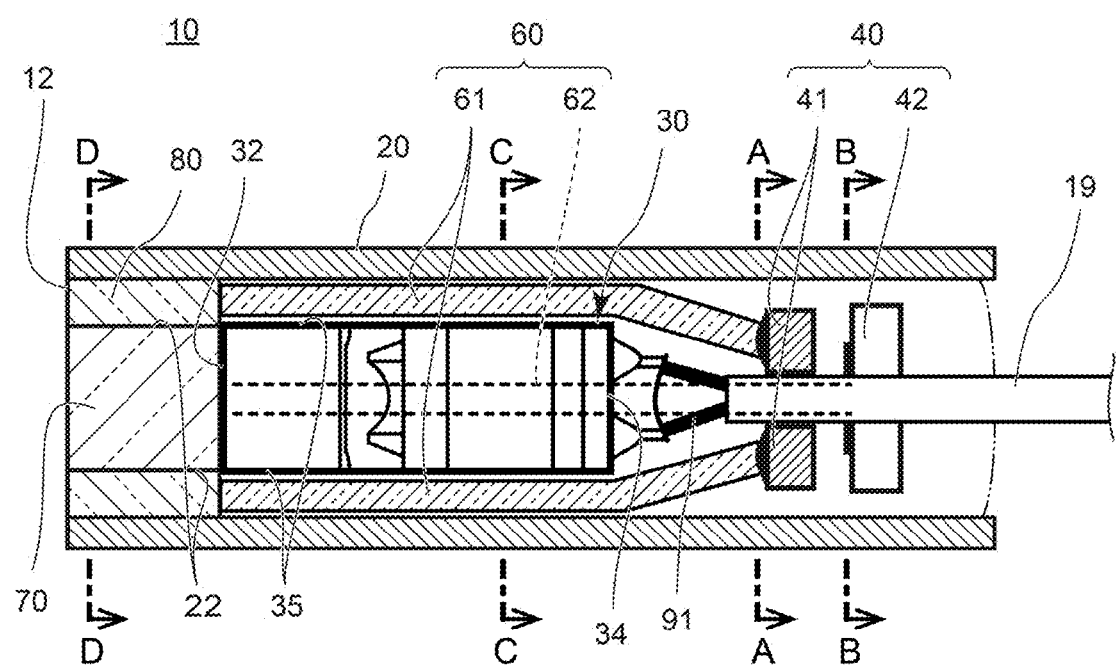
FIG. 3 is a cross-sectional side view of a camera head according to the same.
Figure 4:
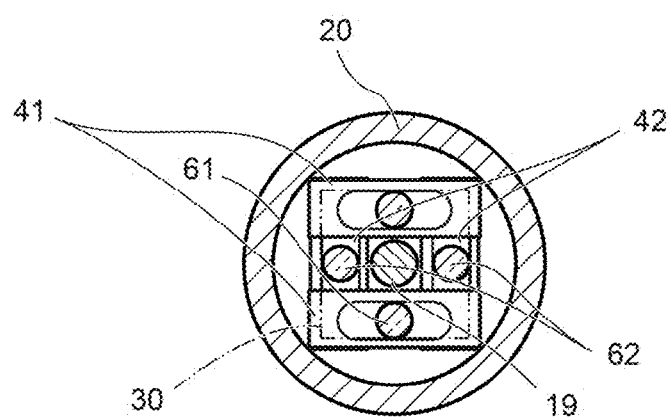
FIG. 4 is a cross-sectional view taken along a line A-A in FIG. 3.
Figure 5:
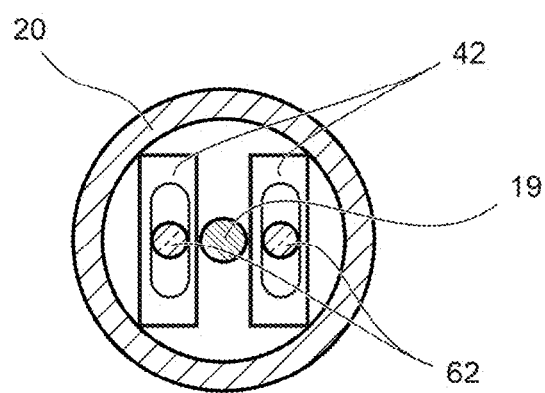
FIG. 5 is a cross-sectional view taken along a line B-B in FIG. 3.
Figure 6:
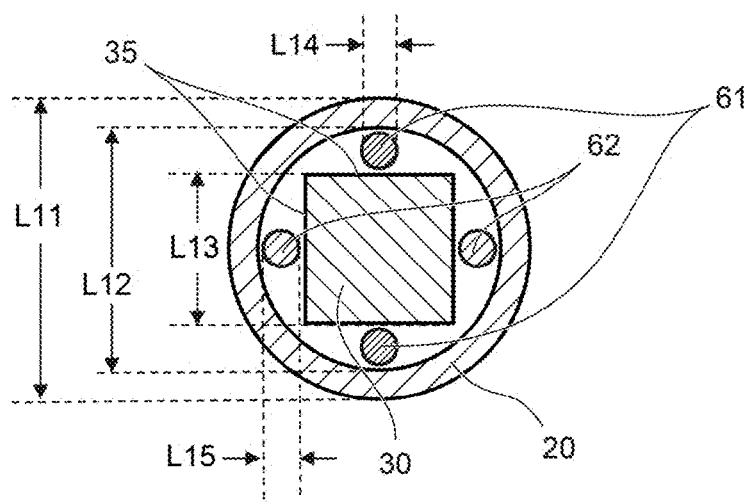
FIG. 6 is a cross-sectional view taken along a line C-C in FIG. 3.
Figure 7:
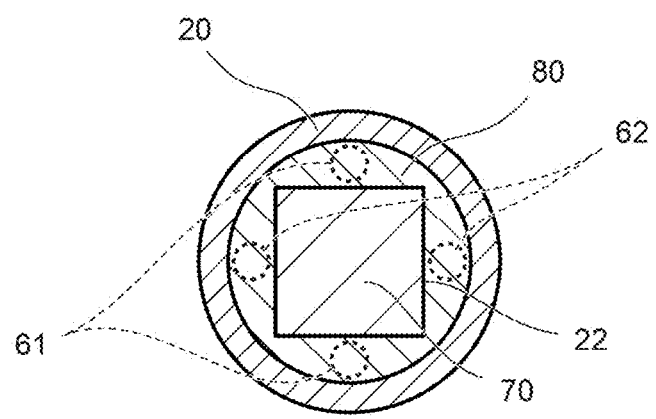
FIG. 7 is a cross-sectional view taken along a line D-D in FIG. 3.

FIG. 3 is a cross-sectional side view of the camera head 10 according to the same. FIG. 4 is a cross-sectional view taken along the line A-A in FIG. 3. FIG. 5 is a cross-sectional view taken along the line B-B in FIG. 3. FIG. 6 is a cross-sectional view taken along the line C-C in FIG. 3. FIG. 7 is a cross-sectional view taken along the line D-D in FIG. 3.

In these figures and in similar cross-sectional views below, hatching indicates cross-sections of members, but for ease of illustration, cross-sections of not all members are necessarily hatched.

As shown in the figures, the camera head 10 has an overall elongated shape. In the present embodiment, the camera head 10 as a whole has a substantially cylindrical shape. Note that the leading end portion and the rear end portion of the camera head 10 may be rounded, or may have partial projections and recesses. FIG. 3 can be said to show a cross-section taken along a plane passing through the central axis of the camera head 10.

The camera head 10 includes, for example, a sleeve 20, the camera module 30, the light source units 40, a light guide unit 60, and filters 70 and 80. An illumination filter 70 and an imaging filter 80 are provided as the filters 70 and 80 in the present embodiment.

The sleeve 20 is formed into a cylindrical shape. It may be said that the sleeve 20 is formed into a tubular shape. There is no restriction on the material of the sleeve 20. Any material such as metal, ceramic, or resin may be used. In the present embodiment, each unit of the camera head 10 is housed in the sleeve 20. It may be said that each unit of the camera head 10 is located inside the sleeve 20. It may also be said that each unit of the camera head 10 is located inside the inner circumferential surface of the sleeve 20 in the radial direction (the direction toward or away from the central axis of the camera head 10). In the present embodiment, the inner circumferential surface of the sleeve 20 has a cylindrical shape.

The camera module 30 is a module in which an imaging element and an optical system such as a lens are packaged. For example, a module having a known structure can be used as the camera module 30. The camera module 30 has a structure in which a light receiving unit 32, which is located on the leading end side and into which light to be captured enters, an optical system including the lens, etc., and the imaging element are lined up in the longitudinal direction of the camera head 10 (the left-right direction in FIG. 3). Wires 91 connected to the imaging element are connected to a rear end portion 34 of the camera module 30, i.e., the rear end portion 34 of the imaging element. The wires 91 can be bundled into a cable 19 and connected to the image acquisition device 100 or the like.

In the present embodiment, the camera module 30 as a whole has a rectangular prism shape formed such that the longitudinal direction of the camera head 10 corresponds to the height direction. That is to say, the outer surface (the circumference-side surface) of the camera module 30 is constituted roughly by four flat portions 35 that are substantially flat. The cross-section of the camera module 30 is substantially square, but may have another rectangular or quadrangular shape. Note that the camera module 30 is not limited to such a shape and may have any shape as long as it includes a columnar portion having a polygonal columnar shape. The flat portions 35 may be said to be planar side surfaces of the columnar portion.

For example, the camera module 30 is not limited to having a quadrangular column shape, and may be formed to have a triangular column shape or another polygonal column shape. That is to say, the circumference-side surface of the camera module 30 may be constituted by three or more flat portions 35 that are substantially flat. In addition, the camera module may also have a three-dimensional shape called a torsion column (helical column), in which the bottom surface rotates around a central axis along the height direction. The camera module 30 may be cylindrical or have another shape.

Each light source unit 40 is a light source that irradiates the imaging area when imaging is performed using the camera head 10. For example, each light source unit 40 may be, but is not limited to, an LED chip. For example, each light source unit 40 may be another type of light source, such as a laser diode. For example, electrical wires (not shown) passed through the cable 19 are connected to the light source units 40, and each light source unit 40 is configured to illuminate when power is supplied from the image acquisition device 100 or the like. For example, each light source unit 40 as a whole has a rectangular parallelepiped shape as described below, but is not limited to having such a shape, and may have another shape, such as a cylindrical shape, a coin shape, a flat plate shape, or the like.

The camera head 10 includes two or more light source units 40. For example, in the present embodiment, four light source units 40 are provided. Two of the four light source units 40 are the first light source units 41, and the other two are the second light source units 42. Each of the first light source units 41 and the second light source units 42 as a whole is, for example, an LED chip having a substantially rectangular parallelepiped shape and is disposed to emit light from the front surface thereof. The first light source units 41 and the second light source units 42 are configured to emit light of wavelengths different from each other. In the present embodiment, the first light source units 41 and the second light source units 42 are provided, so that it is possible to simplify the structure of the light guide unit 60 that guides light from each light source unit forward. In addition, it is easier to adjust the amount of light emitted from the camera head 10 for each wavelength.

Note that the number of the light source units 40 is not limited to the number mentioned above. It is sufficient that two or more light source units 40 are provided. Of the two or more light source units 40, at least two are preferably configured to emit light of wavelengths different from each other, as in the present embodiment. For example, the camera head 10 may be provided with one first light source unit 41 and one second light source unit 42. Note that the present invention is not limited to such a configuration and may have a configuration in which the first light source units 41 and the second light source units 42 emit light of the same wavelength. Alternatively, it is also possible to adopt a configuration in which one light source unit 40 or two or more light source units 40 that emit light of the same wavelength are provided, and the light emitted from the light source unit(s) 40 is passed through filters that transmit light within wavelength bands different from each other so that light of two or more wavelengths can be transmitted from the camera head 10.

As shown in the figure, each light source unit 40 is disposed at a position farther from the leading end portion 12 than the camera module 30 is in the longitudinal direction. That is to say, each light source unit 40 is disposed rearward of the camera module 30. It may be said that each light source unit 40 is located behind the camera module 30 when viewed from the front in the longitudinal direction of the camera head 10 (the leading end portion 12 side). Since each light source unit 40 is located away from the leading end portion 12, heat generated by each light source unit 40 is less likely to be transmitted to the leading end portion 12, and is prevented from affecting the subject. In addition, each light source unit 40 is disposed at a position where a portion of the light source unit 40 overlaps the camera module 30 when viewed from the front in the longitudinal direction. As a result, each unit of the camera head 10 can be housed in the sleeve 20 with a smaller diameter, and the camera head 10 can be made smaller in diameter (thinner in diameter).

In addition, in the camera head 10, at least two light source units 40 of the light source units 40 are located at different positions in the longitudinal direction. The rear end of at least one light source unit 40 of the at least two light source units 40 is located forward of the front end of the other at least one light source unit 40. Since at least two light source units 40 are located at different positions in the longitudinal direction in this manner, the light source units 40 can be housed in the sleeve 20 with a smaller diameter. In other words, the diameter of the camera head 10 can be made smaller. In order to make the diameter further smaller, the at least two light source units 40 can be disposed so as to partially overlap each other when viewed from the front in the longitudinal direction.

In addition, the at least two light source units 40 are located at different positions in the circumferential direction. Since the at least two light source unit 40 are located at different positions in the circumferential direction, the structure for guiding the light from each light source unit 40 to the leading end portion 12 can be simplified as will be described later.

More specifically, in the present embodiment, in the camera head 10, the two first light source units 41 are located forward of the two second light source units 42. In other words, the camera module 30, the two first light source units 41, and the two second light source units 42 are disposed in this order in the longitudinal direction from the leading end portion 12 side. It can be said that the two first light source units 41 are sandwiched between the rear end portion 34 of the camera module 30 and the front end portions of the second light source units 42.

As shown in FIG. 4, in the present embodiment, the two first light source units 41 are disposed radially outside the cable 19 so that the cable 19 is sandwiched between the two first light source units 41. The two first light source units 41 are disposed such that the long sides thereof are substantially parallel to each other when viewed from the front in the longitudinal direction. As shown in FIG. 5, the two second light source units 42 are also disposed radially outside the cable 19 so that the cable 19 is sandwiched between the two second light source units 42. The two second light source units 42 are disposed such that the long sides thereof are substantially parallel to each other when viewed from the front in the longitudinal direction.

In the present embodiment, the first light source units 41 and the second light source units 42 are disposed so that the long sides of the first light source units 41 and the long sides of the second light source units 42 are orthogonal to each other when viewed from the front in the longitudinal direction. That is to say, the first light source units 41 and the second light source units 42 are located at different positions in the circumferential direction. In addition, the first light source units 41 and the second light source units 42 are disposed so as to partially overlap each other when viewed from the front in the longitudinal direction. Here, the expressions "parallel" and "orthogonal" do not necessarily mean that the units strictly have such a relationship. The units need only be substantially parallel or substantially orthogonal to each other. Note that the positional relationship between the first light source units 41 and the second light source units 42 when viewed from the front in the longitudinal direction is not limited to the relationship mentioned above. When viewed from the front in the longitudinal direction, a straight line overlapping the long sides of the first light source units 41 and a straight line overlapping the long sides of the second light source units 42 may intersect at a predetermined angle. It is preferable that two or more light source units 40 at different positions in the longitudinal direction are disposed so that the positions from which light is emitted are different from each other when viewed from the front in the longitudinal direction. Such an arrangement allows the light guide unit 60 to have a relatively simple configuration. For example, when optical fibers are used as the light guide unit 60 as described below, the optical fibers can be easily routed. When the two or more light source units 40 are disposed at different positions in the longitudinal direction, for example, it is possible to adopt a configuration in which the light source units 40 are located so as to be shifted one after another by a predetermined angle about the center of the camera head 10 when viewed from the front in the longitudinal direction.

Note that one first light source unit 41 and one second light source unit 42 may be disposed at substantially the same position in the longitudinal direction, and the other first light source unit 41 and the other second light source unit 42 may be disposed rearward thereof. Alternatively, the first light source units 41 may be located on the rear side, and the second light source units 42 may be located on the front side. It is sufficient that either the first light source units 41 or the second light source units 42 are located forward or rearward of the others.

It is preferable that the rear end portion 34 of the camera module 30 and the first light source unit 41 that is closest to the leading end portion 12 among the light source units 40 are close to each other. In the present embodiment, a portion of the leading end portion 12 side front surface of the light source unit 40 that is located closest to the leading end portion 12 faces the rear end portion 34 of the camera module 30 in the longitudinal direction. With such a structure, i.e., a structure in which portions of the light source units 40 overlap the camera module 30 when viewed from the front in the longitudinal direction as shown in FIG. 4, the camera head 10 can be made even smaller.

The light guide unit 60 is disposed radially outside the outer surface of the camera module 30. In the present embodiment, the light guide unit 60 is disposed between the flat portions 35 of the camera module 30 and the inner circumferential surface of the sleeve 20. The light guide unit 60 guides the light emitted from each of the light source units 40 to the vicinity of the leading end portion 12 so that the imaging area can be irradiated with the light. It can be said that the light guide unit 60 guides the light to the vicinity of the leading end portion 12. It can also be said that the light guide unit 60 serves to guide for guiding the light to the vicinity of the leading end portion 12. The vicinity of the leading end portion 12 may include the leading end portion 12. In the present embodiment, an illumination filter 80 through which the guided light passes is provided in the leading end portion 12, and the light guide unit 60 is configured to guide the light to the vicinity of a light entrance portion where light enters the illumination filter 80. That is to say, the light entrance portion where light enters the illumination filter 80 is included in the vicinity of the leading end portion 12.

Note that when the light guide unit 60 guides the light emitted from the light source units 40 behind the camera module 30 to the vicinity of the leading end portion, it can also be said that the light guide unit 60 guides the light forward so that the light is emitted to a position in front of the camera module 30.

In the present embodiment, the light guide unit 60 includes optical fibers. Note that elements other than optical fibers, for example, optical waveguides or the like made of resin, glass, or the like, may be used.

In the present embodiment, the light guide unit 60 includes four optical fibers respectively corresponding to the light source units 40. Of the four optical fibers, two are referred to as first light guide units 61 and the other two are referred to as second light guide units 62. The two first light guide units 61 respectively correspond to the two first light source units 41, and the two second light guide units 62 respectively correspond to the two second light source units 42. Note that, for one light source unit 40, two or more elements such as optical fibers may be provided to guide light so that the light is emitted from different positions in the radial or circumferential direction.

In the present embodiment, the four optical fibers of the light guide unit 60 are disposed around the camera module 30 so as to be spaced apart from each other in the circumferential direction and lined up in the circumferential direction. The optical fibers are lined up at substantially equal intervals in the circumferential direction. That is to say, the four optical fibers are lined up at approximately 90-degree intervals in the circumferential direction.

More specifically, as shown in FIG. 6, the first light guide units 61 and the second light guide units 62 are lined up alternately in the circumferential direction. That is to say, the light guide unit 60 is configured to be capable of irradiating the imaging area with light within a wavelength band from two positions that are spaced apart from each other in the circumferential direction. As a result, the imaging area is relatively uniformly irradiated with the light within the respective wavelength bands of the first light source units 41 and the second light source units 42.

Here, the optical fibers are disposed along the flat portions 35 of the camera module 30. In the present embodiment, one optical fiber is disposed in each of the four spaces formed between the four flat portions 35 and the inner circumferential surface of the sleeve 20. As a result of such an arrangement of the optical fibers, each unit of the camera head 10 can be housed in the sleeve 20 with a smaller diameter, and the camera head 10 can be made smaller in diameter.

An imaging filter 70 and the illumination filter 80 are attached to the leading end portion 12 of the camera head 10.

In the present embodiment, the camera head 10 is configured to be used in bioimaging technology, for example, by irradiating the imaging area with excitation light of a specific wavelength to excite a fluorescent substance and imaging the emitted fluorescence. To enable the camera head 10 to be used for such applications, the imaging filter 70 is disposed on the leading end side of the camera module 30, and the illumination filter 80 is disposed on the leading end side of the light guide unit 60.

The illumination filter 80 is, for example, an excitation light filter. The illumination filter 80 allows only light in a specific wavelength range of the light guided by the light guide unit 60 to pass therethrough and irradiates the imaging area with the light. This light acts on and excites fluorescent substances or fluorescent markers in tissues or the like in the imaging region. The imaging filter 70 is, for example, a fluorescent filter. The imaging filter 70 is configured to allow only fluorescence in a specific wavelength range different from the excitation light to pass therethrough, and allows only a certain fluorescence signal generated after excitation to enter the light receiving unit 32 of the camera module 30 with high precision.

The imaging filter 70 is fixed to the camera module 30 so as to cover the front of the light receiving unit 32. The illumination filter 80 is disposed forward of the light guide unit 60 so as to have a shape that closes the gap between the imaging filter 70 and the inner circumferential surface of the sleeve 20. That is to say, in the present embodiment, the leading end portion 12 of the camera head 10 is sealed with the filters 70 and 80. Note that the rear end portion of the camera head 10 is sealed with a bonding material or the like as indicated by the two-dot chain line in FIG. 3, for example. However, the present invention is not limited to such a configuration.

Note that the filters 70 and 80 are not limited to those with the properties described above. Filters with properties appropriate for their applications may be used. In addition, one or both of the filters 70 and 80 may be omitted. In this case, the leading end portion 12 may be provided with a filter for protection purposes, or no optical elements may be provided in addition to the camera module 30 and the light guide unit 60. The filters 70 and 80 may or may not be so-called optical filters.

As shown in FIG. 7, in the present embodiment, a light blocking structure 22 configured to block light is provided between the filters 70 and 80 so as to prevent light originating from the light emitted from the light source units 40 from directly entering the camera module 30. In other words, the light blocking structure 22 prevents light other than the light entering from the imaging area from entering the camera module 30. The light blocking structure 22 may be provided around the camera module 30, around the light guide unit 60, or the like.

For example, the light blocking structure 22 is a metal film or the like, or a film or the like having light blocking properties, but is not limited to these examples. When the imaging filter 70 or the illumination filter 80 is configured to totally reflect incident light, such a configuration may be regarded as the light blocking structure 22. The light blocking structure 22 may also be a filler having light blocking properties that is applied or filled into the gaps between members. For example, the filler may be a mixture of an adhesive or a resin or the like that cures by a chemical reaction, and a pigment or the like. The light blocking structure 22 is not limited to these examples, and various structures that prevent the incidence of light other than the light entering from the imaging area can be used. Depending on the application and configuration of the camera head 10, the light blocking structure 22 may be omitted.

Figure 8:
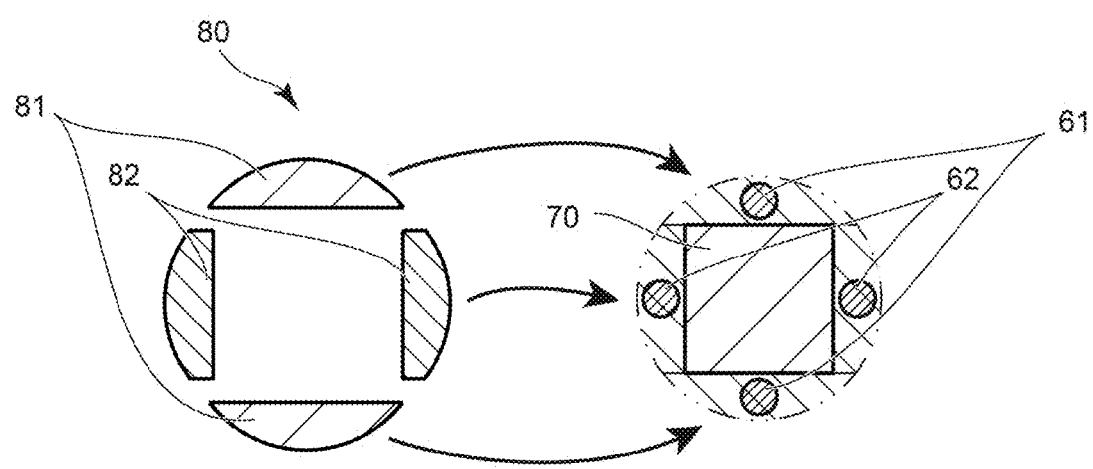
FIG. 8 is a diagram illustrating a configuration of an illumination filter for the camera head according to the same.

FIG. 8 is a diagram illustrating the configuration of the illumination filter 80 of the camera head 10.

Here, in the present embodiment, the illumination filter 80 includes first excitation light filters 81 corresponding to the first light source units 41 and second excitation light filters 82 corresponding to the second light source units 42. Thus, the illumination filter 80 is configured to be capable of emitting excitation light of different wavelengths corresponding to the light emitted from the first light source units 41 and the second light source units 42.

As shown in FIG. 8, for example, the illumination filter 80 is formed by combining four members, namely the two first excitation light filters 81 disposed forward of the first light guide units 61, and the two second excitation light filters 82 disposed forward of the second light guide units 62. Adjacent filters in the circumferential direction of the filters 81 and 82 are attached to each other to form one illumination filter 80. Note that the configuration of the illumination filter 80 is not limited to this example.

In the present embodiment, the imaging filter 70 and the illumination filter 80 are joined together. The camera module 30 is fixed to the imaging filter 70. The light guide unit 60 is fixed to the illumination filter 80. As a result, the camera module 30 and the light guide unit 60 are integrated into one piece. This makes it possible to easily manufacture the camera head 10.

As described above, by disposing the camera module 30 and two or more light source units 40 at different positions in the longitudinal direction and spaced apart from each other in the longitudinal direction instead of disposing them on the same cross section, it is possible to form a small camera head 10 with built-in light sources. More specifically, the camera head 10 capable of irradiating the imaging area with light from each of the first light source units 41 and the second light source units 42 can be made even smaller. In the present embodiment, it can be said that the diameter of the camera head 10 can be particularly reduced.

In addition, since the camera head 10 can be formed with built-in light sources, there is no need to bundle optical fibers or the like with the cable 19, and the flexibility of the cable 19 can be improved.

The fact that the diameter of the camera head 10 can be reduced will now be described with specific dimensional examples.

Figure 9:
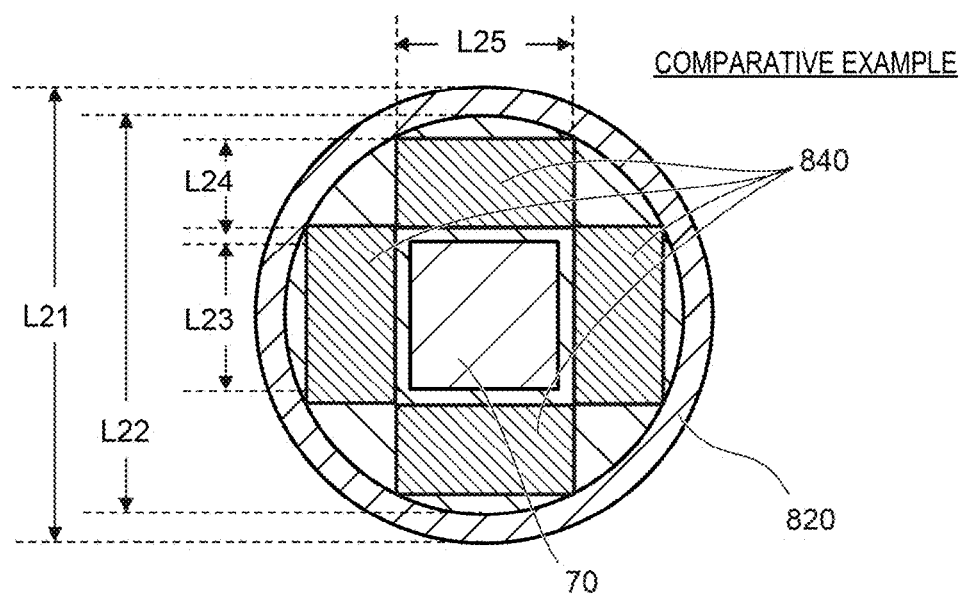
FIG. 9 is a diagram illustrating an example of a configuration of a camera head according to one comparative example of the present embodiment.

FIG. 9 is a diagram illustrating an example of a configuration of a camera head according to one comparative example of the present embodiment.

FIG. 9 shows an example of a configuration in which, for example, 0201 size LED chips are disposed in the leading end portion as light source units 840. In order to ensure that light is emitted uniformly, the light source units 840 are disposed at four positions so as to surround the imaging filter 70 having the same size as that in the present embodiment. Here, each 0201 size element has two sides with lengths of 0.6 mm and 0.3 mm when viewed from the front.

In this comparative example, the dimensions shown in the figure are as follows: L21 is 1.52 mm; L22 is 1.31 mm; L23 is 0.5 mm; L24 is 0.3 mm; and L25 is 0.6 mm.

That is to say, the inner diameter of a sleeve 820 is 1.31 mm, and when the thickness of the sleeve 820 is approximately 0.1 mm, the outer diameter of the sleeve 820 is 1.52 mm. That is to say, the outer diameter of the camera head in this comparative example is 1.52 mm.

On the other hand, in the present embodiment, the specific dimensional examples shown in FIG. 6 are as follows. Here, it is assumed that each of the optical fibers for the light guide unit 60 has a diameter of 0.125 mm. In this case, L11 is 1.00 mm. L12 is 0.8 mm. L13 is 0.5 mm. L14 is 0.125 mm. L15 is 0.125 mm.

When a sleeve 20 of such a size is used and 0201 size LED chips are used as the light source units 40, the light source units can be disposed rearward of the camera module 30, for example at different positions in the longitudinal direction.

In this manner, in the present embodiment, the camera head 10 can be formed to have a thinner and smaller outer diameter than the comparative example.

If the camera head 10 can be made smaller in size in this way, the camera head 10 and the imaging system 1 using the same will become more useful in several applications.

Figure 10:
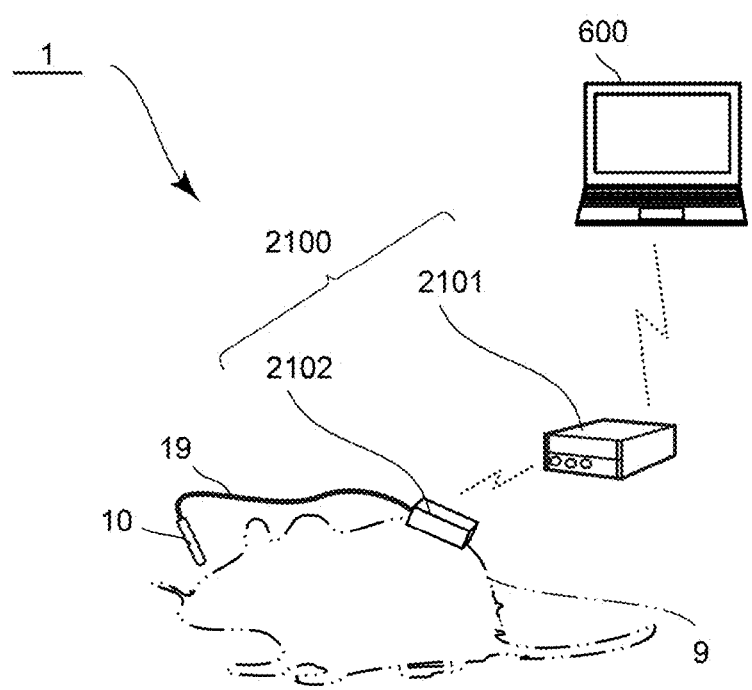
FIG. 10 is a diagram illustrating a use example of the imaging system according to the present embodiment.

FIG. 10 is a diagram illustrating a use example of the imaging system 1 according to the present embodiment.

FIG. 10 shows a use example of a case in which an image capturing a tissue condition image of a test animal 9 is acquired using the imaging system 1. Here, the imaging system 1 is constituted by the camera head 10 and an image acquisition device 2100 to which the camera head 10 is connected via the cable 19. The image acquisition device 2100 is constituted by a transmitting and receiving device 2102 that can be small enough to be attached to the test animal 9, and a main device 2101 that has the same functions as the image acquisition device 100 described above. That is to say, in the example shown in the figure, the image acquisition device 2100 can wirelessly capture images showing the imaging results of the camera head 10.

As described above, the camera head 10 can be formed with a small diameter of about 1 mm. Such a configuration makes it possible to perform an experiment in a less invasive manner than before with respect to the test animal 9 in which the camera head 10 is embedded. This configuration also allows continuous imaging while the camera head 10 remains embedded in the test animal 9. Therefore, this configuration allows experiments to be performed under conditions and in observation patterns that are difficult to achieve with conventional large camera heads.

Descriptions of Modifications

The above embodiment shows an example of the camera head 10 configured to be capable of emitting light of two different wavelengths, but the present invention is not limited to this example.

Figure 11:
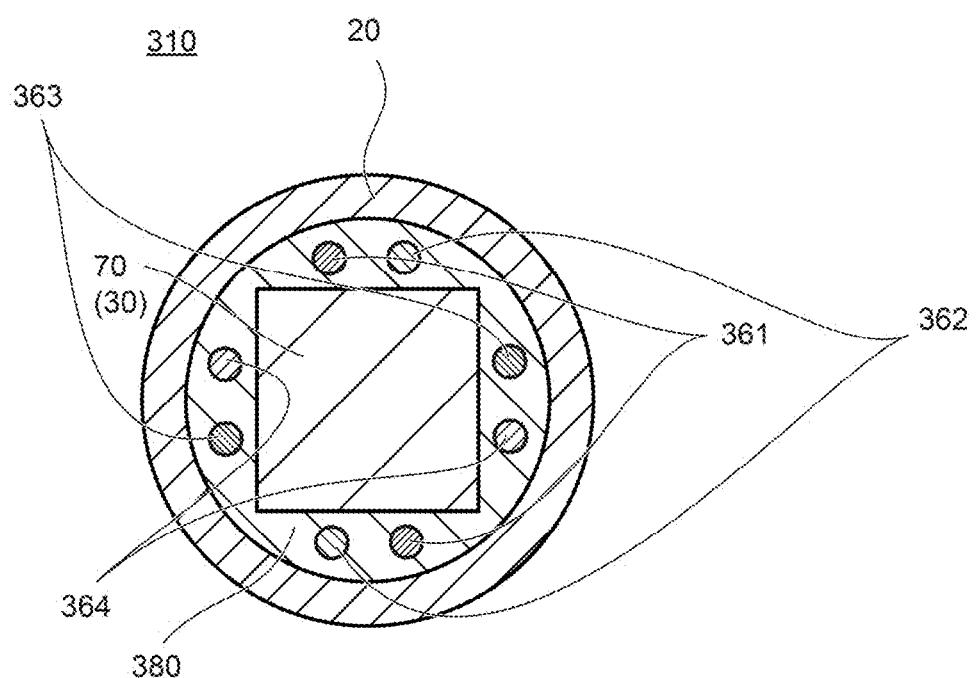
FIG. 11 is a diagram illustrating an example of a configuration of a camera head according to a first modification of the embodiment of the present invention.

FIG. 11 is a diagram illustrating an example of a configuration of a camera head according to a first modification of the embodiment of the present invention.

The diagram shows a cross-sectional view of the vicinity of a leading end portion 12 of a camera head 310 configured to be capable of emitting, for example, four different types of light.

The camera head 310 includes, for example, four types of optical fibers, 361, 362, 363, and 364, as light guide units corresponding to four light source units (not shown) that emit light within wavelength bands different from each other. Two optical fibers 361, two optical fibers 362, two optical fibers 363, and two optical fibers 364 are provided. That is to say, a total of eight optical fibers 361, 362, 363, and 364 are provided as light guide units. The optical fibers 361, 362, 363, and 364 are disposed radially outside the camera module 30 and are lined up in the circumferential direction so as to surround the camera module 30. The pairs of optical fibers 361, 362, 363, or 364, each pair corresponding to light from a different light guide unit, are respectively disposed in the four gaps between the camera module 30 and the inner circumferential surface of the sleeve 20.

As a result of the large number of optical fibers 361, 362, 363, and 364 disposed in this manner, the camera head 310 can be formed into a relatively small size.

In the present modification, of the optical fibers 361, 362, 363, and 364, each pair of optical fibers provided for guiding light within one wavelength band is disposed around the camera module 30 so as to be spaced apart from each other in the circumferential direction. More specifically, as shown in the diagram, when viewed from the front in the longitudinal direction, the two optical fibers 361 that guide light within a first wavelength band are disposed at positions that are point-symmetric with respect to the center of the camera head 310. Similarly, the two optical fibers 362 that guide light within the second wavelength band, the two optical fibers 363 that guide light within the third wavelength band, and the two optical fibers 364 that guide light within the fourth wavelength band are each disposed in a point-symmetric relationship with respect to the center of the camera head 310. However, the present invention is not limited to such a configuration and, for example, two optical fibers that guide light within a wavelength band may be respectively disposed in two of the four gaps between the camera module 30 and the inner surface of the sleeve 20 that are not adjacent to each other.

As a result of the optical fibers 361, 362, 363, and 364 disposed in this manner, the imaging area can be relatively uniformly irradiated with light within each wavelength band.

Note that, in the camera head 310, a filter 380 is provided instead of the illumination filter 80. The properties and functions of the filter 380 can be adjusted as required.

Figure 12:
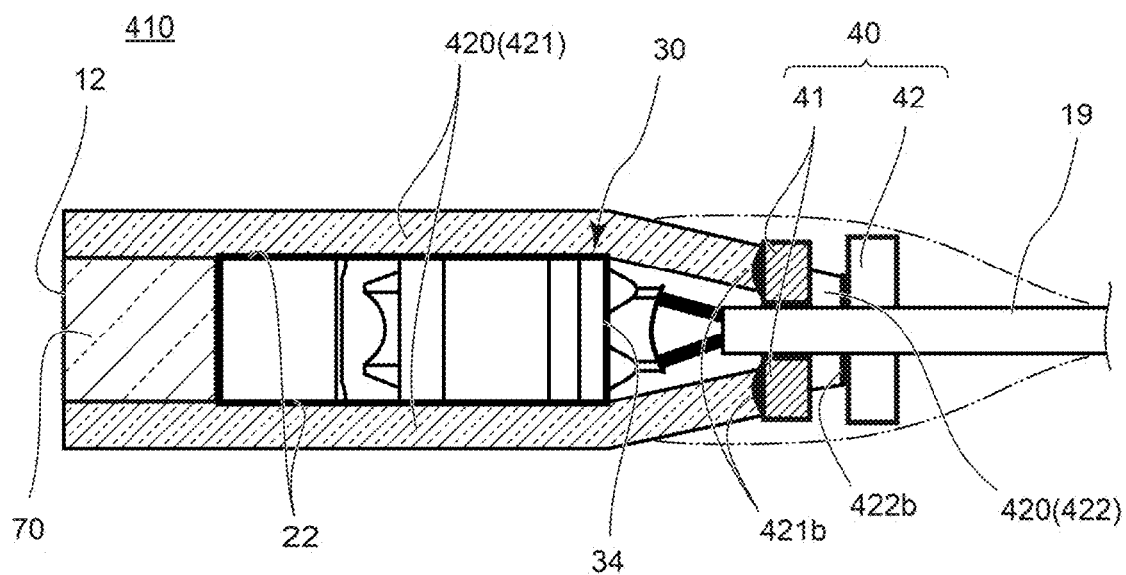
FIG. 12 is a diagram illustrating an example of a configuration of a camera head according to a second modification of the embodiment of the present invention.

FIG. 12 is a diagram illustrating an example of a configuration of a camera head according to a second modification of the embodiment of the present invention.

The diagram shows a cross-sectional side view of a camera head 410 in the same manner as in FIG. 3.

The camera head 410 includes the camera module 30, the light source units 40, the imaging filter 70, and so on, which have the same configurations as in the camera head 10 according to the embodiment described above. That is to say, the imaging filter 70, the camera module 30, the first light source units 41, and the second light source units 42 are lined up in this order in the longitudinal direction from the leading end portion 12 side at different positions from each other.

In the camera head 410, a sleeve 420 is provided in place of the sleeve 20. The camera module 30 and the imaging filter 70 are housed in the sleeve 420.

The sleeve 420 is a light transmissive member, and is configured to function as a light guide unit that guides the light from the light source units 40 toward the leading end portion 12. That is to say, in the present modification, the light guide unit is constituted by the entire sleeve 420. The sleeve 420 functioning as a light guide unit can be made of, for example, a light transmissive resin or the like, but is not limited to this example. Note that the light guide unit may be constituted by a portion of the sleeve 420. For example, only the portion of the sleeve 420 that functions as a light guide unit may be configured to serve as an optical waveguide.

In the present modification, the sleeve 420 is formed, for example, by combining a first member 421 including, on the rear end portion side, light entrance portions 421b connected to the first light source units 41, and a second member 422 including, on the rear end portion side, light entrance portions 422b connected to the second light source units 42. This configuration allows the light emitted from the first light source units 41 and the second light source units 42 to be emitted independently.

Note that the sleeve 420 may be molded as a single member including both the light entrance portions 421b and 422b. Alternatively, the sleeve 420 may be formed to house the light source units 40. That is to say, the sleeve 420 need only include the light entrance portions 421b and 422b as portions thereof, and the light entrance portions 421b and 422b need not be provided at the rear end portion of the sleeve 420.

In this manner, by using the sleeve 420 that functions as a light guide unit, the camera head 410 can be made smaller.

Others

In the embodiment described above, a single computer or a plurality of computers may be used. That is to say, centralized processing may be performed, or distributed processing may be performed.

In addition, in the embodiment described above, two or more components present in one device may be physically realized with a single medium.

In the embodiment described above, each component may be constituted by dedicated hardware. Alternatively, components that can be realized with software may be realized by executing a program. For example, each component can be realized by a program execution unit such as a CPU reading and executing a software program recorded on a recording medium such as a hard disk or a semiconductor memory. During execution, the program execution unit may execute the program while accessing a storage unit or a recording medium. The program may be downloaded from a server or the like and executed, or a program recorded on a predetermined recording medium (for example, an optical disk, a magnetic disk, a semiconductor memory, or the like) may be read out and executed. In addition, this program may also be used as a program constituting a program product. The program may be executed by a single computer or a plurality of computers. That is to say, centralized processing may be performed, or distributed processing may be performed.

In addition, in the embodiment described above, each type of processing (each function) may be realized as centralized processing by a single device (system), or may be realized as distributed processing by a plurality of devices (in this case, the entire system constituted by a plurality of devices performing distributed processing can be considered as a single "device").

In addition, in the embodiment described above, the transfer of information between the components may be performed, for example, by one component outputting information and the other component receiving information if the two components transferring the information are physically different, or, if the two components transferring the information are physically the same, the transfer of information between the components may be performed by transitioning from a processing phase corresponding to one component to a processing phase corresponding to the other component.

In addition, in the embodiment described above, information related to the processing performed by each component, for example information accepted, acquired, selected, generated, transmitted, or received by each component, and information such as thresholds, formulas, addresses, etc. used by each component in its processing, may be stored temporarily or for a long period of time on a recording medium (not shown), even if not explicitly stated in the above description. The accumulation of information in the recording medium (not shown) may be performed by each component or by an accumulation unit (not shown). The reading of information from the recording medium (not shown) may be performed by each component or by a reading unit (not shown).

The present invention is not limited to the embodiment described above, and various modifications are possible, which are also included within the scope of the present invention.

The components of the embodiment and modifications described above may be combined as appropriate to form an embodiment. For example, each of the components of the embodiment and modifications described above may be replaced or combined with components of other modifications or the like as appropriate. In addition, some of the components or functions of the embodiment and modifications described above may be omitted.

INDUSTRIAL APPLICABILITY

As described above, the camera head according to the present invention has the effect of enabling the camera head to be made even smaller, and is useful as a camera head or the like.

The invention claimed is:

1. A camera head that has an elongated shape and is used for imaging an imaging area located in a vicinity of a leading end portion in a longitudinal direction, comprising:
   a camera module;
   two or more light source units disposed at positions farther from the leading end portion than the camera module is in the longitudinal direction; and
   a light guide unit disposed radially outside an outer surface of the camera module and configured to guide light emitted from each of the two or more light source units to the vicinity of the leading end portion so that the imaging area is irradiated with the light,
   wherein at least two light source units of the two or more light source units are disposed at different positions in the longitudinal direction,
   wherein the light guide unit includes two or more optical fibers respectively corresponding to at least two light source units of the two or more light source units, and the two or more optical fibers are disposed around the camera module so as to be spaced apart from each other in a circumferential direction and lined up in the circumferential direction, and
   wherein, of the two or more light source units, at least two light source units located at different positions in the longitudinal direction are disposed so as to partially overlap each other when viewed from a front in the longitudinal direction.

2. The camera head according to claim 1, wherein at least two light source units of the two or more light source units are configured to emit light of wavelengths different from each other.

3. The camera head according to claim 1, wherein, of the two or more optical fibers, two or more optical fibers provided for guiding light within one wavelength band are disposed around the camera module so as to be spaced apart from each other in the circumferential direction, and
   the light guide unit is configured to irradiate the imaging area with the light within the one wavelength band from two or more positions that are spaced apart from each other in the circumferential direction.

4. The camera head according to claim 1,
wherein the camera module has a columnar portion having a polygonal columnar shape, and
the two or more optical fibers are disposed along planar side surfaces of the columnar portion.

5. The camera head according to claim 1, further comprising
a sleeve formed into a tubular shape,
wherein the camera module, the light source units, and the light guide unit are housed in the sleeve.

6. The camera head according to claim 1, further comprising
a sleeve formed into a tubular shape,
wherein the sleeve is a light transmissive member,
the light guide unit is a portion or an entirety of the sleeve, and
the camera module is housed in the sleeve.

7. The camera head according to claim 1,
wherein the camera module and the light guide unit are integrated into one piece.

8. A camera head that has an elongated shape and is used for imaging an imaging area located in a vicinity of a leading end portion in a longitudinal direction, comprising:
a camera module;
two or more light source units disposed at positions farther from the leading end portion than the camera module is in the longitudinal direction; and
a light guide unit disposed radially outside an outer surface of the camera module and configured to guide light emitted from each of the two or more light source units to the vicinity of the leading end portion so that the imaging area is irradiated with the light,
wherein at least two light source units of the two or more light source units are disposed at different positions in the longitudinal direction,
wherein the light guide unit includes two or more optical fibers respectively corresponding to at least two light source units of the two or more light source units, and
the two or more optical fibers are disposed around the camera module so as to be spaced apart from each other in a circumferential direction and lined up in the circumferential direction, and
wherein each of the two or more light source units is disposed at a position farther from the leading end portion than the camera module is in the longitudinal direction at which a portion thereof overlaps the camera module when viewed from a front in the longitudinal direction.

9. The camera head according to claim 1,
wherein, of the two or more light source units, at least two light source units located at different positions in the longitudinal direction are disposed so that positions from which light is emitted are different from each other when viewed from a front in the longitudinal direction.

10. The camera head according to claim 1, further comprising
a cable extending rearward from the camera module, and including a signal line for communication with the camara module,
wherein at least two light source units of the two or more light source units are disposed so as to sandwich the cable when viewed from a front in the longitudinal direction.

11. A camera head that has an elongated shape and is used for imaging an imaging area located in a vicinity of a leading end portion in a longitudinal direction, comprising:
a camera module;
two or more light source units disposed at positions farther from the leading end portion than the camera module is in the longitudinal direction;
a light guide unit disposed radially outside an outer surface of the camera module and configured to guide light emitted from each of the two or more light source units to the vicinity of the leading end portion so that the imaging area is irradiated with the light;
an imaging filter disposed at a position that is on a leading end side of the camera head and on a leading end side of the camera module so as to cover a front of a light receiving portion;
an illumination filter disposed at a position that is on a leading end side of the camera head and on a leading end side of the light guide unit; and
a light blocking structure provided between the imaging filter and the illumination filter and configured to block light,
wherein at least two light source units of the two or more light source units are disposed at different positions in the longitudinal direction, and
wherein the light guide unit includes two or more optical fibers respectively corresponding to at least two light source units of the two or more light source units, and the two or more optical fibers are disposed around the camera module so as to be spaced apart from each other in a circumferential direction and lined up in the circumferential direction.

12. An imaging system comprising:
the camera head according to claim 1; and
an image acquisition device connected to the camera head and configured to acquire an image captured by the camera head.

13. The camera head according to claim 8,
wherein at least two light source units of the two or more light source units are configured to emit light of wavelengths different from each other.

14. The camera head according to claim 8,
wherein, of the two or more optical fibers, two or more optical fibers provided for guiding light within one wavelength band are disposed around the camera module so as to be spaced apart from each other in the circumferential direction, and
the light guide unit is configured to irradiate the imaging area with the light within the one wavelength band from two or more positions that are spaced apart from each other in the circumferential direction.

15. The camera head according to claim 8,
wherein the camera module has a columnar portion having a polygonal columnar shape, and
the two or more optical fibers are disposed along planar side surfaces of the columnar portion.

16. The camera head according to claim 8, further comprising
a sleeve formed into a tubular shape,
wherein the camera module, the light source units, and the light guide unit are housed in the sleeve.

17. The camera head according to claim 8, further comprising
a sleeve formed into a tubular shape,
wherein the sleeve is a light transmissive member,
the light guide unit is a portion or an entirety of the sleeve, and
the camera module is housed in the sleeve.

18. The camera head according to claim 8,
wherein the camera module and the light guide unit are integrated into one piece.

19. The camera head according to claim 11,
wherein at least two light source units of the two or more light source units are configured to emit light of wavelengths different from each other.

20. The camera head according to claim 11,
wherein, of the two or more optical fibers, two or more optical fibers provided for guiding light within one wavelength band are disposed around the camera module so as to be spaced apart from each other in the circumferential direction, and the light guide unit is configured to irradiate the imaging area with the light within the one wavelength band from two or more positions that are spaced apart from each other in the circumferential direction.

* * * * *